(12) United States Patent
Fraser, III (10) Patent No.: US 11,890,228 B1
(45) Date of Patent: Feb. 6, 2024

(54) VIBRATION INDUCED MEMBRANE RUPTURE

(71) Applicant: Robert W. Fraser, III, Charlotte, NC (US)

(72) Inventor: Robert W. Fraser, III, Charlotte, NC (US)

( * ) Notice: Subject to any disclaimer, the term of this patent is extended or adjusted under 35 U.S.C. 154(b) by 0 days.

(21) Appl. No.: 18/355,857

(22) Filed: Jul. 20, 2023

(51) Int. Cl.
*A61F 9/007* (2006.01)
*A61F 9/013* (2006.01)

(52) U.S. Cl.
CPC .......... *A61F 9/00745* (2013.01); *A61F 9/013* (2013.01)

(58) Field of Classification Search
CPC . A61F 9/00745; A61F 9/013; A61K 41/0047; A61K 9/0009; A61N 7/00; A61N 2007/0039
See application file for complete search history.

(56) References Cited

U.S. PATENT DOCUMENTS

| | | | | |
|---|---|---|---|---|
| 2014/0271901 A1* | 9/2014 | Humayun | ........... | A61K 41/0047 424/94.64 |
| 2016/0151238 A1* | 6/2016 | Crunick | ............. | A61H 23/0218 601/2 |
| 2020/0171307 A1* | 6/2020 | Rockley | ............. | A61N 1/36046 |

OTHER PUBLICATIONS

Patricio A. Pacheco, Advances in Eye Surgery, pp. 118-119, 2016.
Uday Devgan, Cataract Surgery Can Be More Challenging After Vitrectomy, Ocular Surgery News, Oct. 25, 2010, https://www.healio.com/news/opthalmology/20120331/cataract-surgery-can-be-more-challenging-after-vitrectomy.
Rahul K. Reddy et al., Prospective Retinal and Optic Nerve Vitrectomy Evaluation (PROVE) study: findings at 3 months, 7 Clin Opthalmol. 1761, 1761-1769 (2013).
Hiroyasu Shirakawa & Nobuchika Ogino, Idiopathic Epiretinal Membranes with Spontaneous Posterior Vitreous Separation, 197 (2-3) Ophthalmologica 90-94 (1987).

* cited by examiner

*Primary Examiner* — Ashley L Fishback
*Assistant Examiner* — Chima U Igboko
(74) *Attorney, Agent, or Firm* — Shumaker, Loop & Kendrick, LLP; Lloyd J. Wilson (57) ABSTRACT

Methods and systems for vibration induced membrane rupture include an epiretinal membrane (ERM) treatment method that includes providing a vibrational device that includes an interface configured for engaging a closed eyelid of an eye of a patient, where the eye of the patient includes an ERM disposed on an epiretinal surface of a retina of the eye. The interface of the vibrational device engages with the closed eyelid and an instance of vibrational force is applied, via the vibrational device while the interface is engaged with the closed eyelid, to the eyelid, where the vibrational force is capable of propagating through the closed eyelid to the retina of the eye. Further, the instance of vibrational force is applied at predetermined frequency (s) and predetermined intensity(s) for predetermined period(s) of time.

12 Claims, 7 Drawing Sheets

PRIOR ART

VIBRATION INDUCED MEMBRANE RUPTURE

FIELD OF THE INVENTION

This invention relates generally to the field of epiretinal membranes, and more particularly embodiments of the invention relate to systems and methods of vibration induced epiretinal membrane rupture.

BACKGROUND OF THE INVENTION

The retina is a layer of photoreceptor cells, neuronal cells, and glial cells forming the innermost light-sensitive nerve tissue of the eye of most vertebrates. The macular area of the retina is near the center of the retina and processes central vision that is typically needed to distinguish fine details when reading or performing fine hand work. A thin sheet of fibrous tissue forming a semi-transparent membrane can sometimes develop on the inner surface of the retina (i.e., the epiretinal surface). In cases where this thin sheet of fibrous tissue forms near the macular area of the retina, over time it can contract and cause pulling or puckering of the retina, which can result in worsening loss of vision and visual distortion (metamorphopsia). Various terms have been used to describe this thin sheet of fibrous tissue and include epiretinal membrane (ERM), cellophane maculopathy, macular fibrosis, surface wrinkling retinopathy, or macular puckers. For individuals with ERM, the macula neurons work normally, but due to the retinal membrane in which the ERM is embedded getting pulled or puckered, the retinal membrane may fold into waves, thereby causing straight lines to visually appear wavy. Some ERMs are associated with various ocular conditions like prior retinal tears or retinal vascular diseases, whereas other ERMs can be a result of trauma such as ocular surgery. However, the majority of ERMs develop in an eye with no history of prior problems and are labeled idiopathic (of unknown origin).

Fundus biomicroscopy can be used to diagnose an ERM, but often a non-invasive imaging technique called an optical coherence tomography (OCT) is used to diagnose the ERM condition. ADVANCES IN EYE SURGERY 118-119 (Patricio A. Pacheco ed., 2016). Specifically, OCT utilizes light waves to capture cross-sectional images of the retina. OCT has been used to determine that the risk of developing an ERM increases with age, from occurring in approximately 2% of the general population under the age of 60 years to between 12-20% beyond the age of 70. Id. at 116. Once ERM is diagnosed, the most common treatment currently available to treat ERMs that are causing loss of vision and/or vision distortion is a surgical procedure that includes a vitrectomy followed by peeling off the ERM with forceps and, if needed, a micro-vitreoretinal (MVR) blade. During a vitrectomy operation, the surgeon drains the gel-like fluid (vitreous) that fills the eyeball and replaces it with another solution (e.g., gas, saline fluid, etc.), prior to peeling off the ERM. Often dyes are used to better visualize the ERM, and scissors are sometimes necessary to dissect highly-adhered membranes. Draining the vitreous and replacing it with another solution puts oxidative stress on the lens of the eye, which often leads to formation/progression of cataracts. In such cases, the cataracts will often necessitate to a second operation to replace the lens. Patients who undergo cataract surgery after prior retinal surgery are also at higher risk for post-operation complications ("Cataract surgery can be more challenging after vitrectomy," Uday Devgan, Cataract Surgery Can Be More Challenging After Vitrectomy, OCULAR SURGERY NEWS, Oct. 25, 2010, https://www.healio.com/news/opthalmology/20120331/cataract-surgery-can-be-more-challenging-after-vitrectomy. Further, vitrectomy operations can lead to eye infections (endophthalmitis), risk of eye bleeding, retinal tear or detachment, progression of cataracts, problems with eye movement, and/or change in refractive error. In particular, use of forceps and/or a MVR blade to pick and grasp at the ERM can cause damage to subjacent retinal tissue. Id. at 123. There is also a risk that the vitrectomy operation does not successfully improve distorted vision caused by ERMs, which can lead to a repeat vitrectomy surgery. Thus, existing techniques and methods used to treat ERMs have various shortcomings that may not only fail to improve distorted vision caused by ERMs, but may lead to various adverse side effects.

Approximately 225,000 vitrectomies are performed annually in the United States, and the majority are performed to address symptomatic ERMs. Rahul K. Reddy et al., *Prospective Retinal and Optic Nerve Vitrectomy Evaluation (PROVE) study: findings at 3 months*, 7 CLIN OPTHALMOL. 1761, 1761-1769 (2013). As life expectancies lengthen and as the population ages, particularly in the United States, symptomatic ERMs will become more common. Thus, a long-felt need exists in the art for improved systems and methods to treat ERMs.

BRIEF SUMMARY

Shortcomings of the prior art are overcome and additional advantages are provided through the provision of systems and methods of vibration induced epiretinal membrane rupture. Disclosed herein is a method of treating ERMs that includes providing a vibrational device with an interface configured for engaging a closed eyelid of an eye of a patient, where the eye of the patient includes an ERM disposed on the epiretinal surface of the retina of the eye. The interface of the vibrational device is engaged with the closed eyelid, and an instance of vibrational force is applied, via the vibrational device while the interface is engaged with the closed eyelid, to the eyelid, where the vibrational force is capable of propagating through the closed eyelid to the retina of the eye. Further, the instance of vibrational force is applied at one or more predetermined frequencies and one or more predetermined intensities for one or more predetermined periods of time.

Also disclosed is an ERM treatment system that includes an interface configured for engaging a closed eyelid of an eye of a patient, wherein the eye of the patient comprises an ERM disposed on an epiretinal surface of a retina of the eye. The treatment system also includes a motor configured to provide a vibrational force via the interface. The treatment system is configured to perform a method that includes engaging the interface with the closed eyelid, and applying, while the interface is engaged with the closed eyelid, an instance of the vibrational force to the eyelid, wherein the vibrational force is capable of propagating through the closed eyelid to the retina of the eye. Further, the instance of vibrational force is applied at one or more predetermined frequencies and one or more predetermined intensities for one or more predetermined periods of time.

Additional features and advantages are realized through the concepts described herein.

BRIEF DESCRIPTION OF THE DRAWINGS

Aspects described herein are particularly pointed out and distinctly claimed as examples in the claims at the conclusion of the specification. The foregoing and other objects, features, and advantages of the disclosure are apparent from the following detailed description taken in conjunction with the accompanying drawings in which:

DETAILED DESCRIPTION

Aspects of the present invention and certain features, advantages, and details thereof are explained more fully below with reference to the non-limiting examples illustrated in the accompanying drawings. Descriptions of well-known processing techniques, systems, components, etc. are omitted so as to not unnecessarily obscure the invention in detail. It should be understood that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure. Note further that numerous inventive aspects and features are disclosed herein, and unless inconsistent, each disclosed aspect or feature is combinable with any other disclosed aspect or feature as desired for a particular embodiment of the concepts disclosed herein.

The terms "couple," "coupled," "couples," "coupling," "fixed," "attached to," "connect," "connected," and the like should be broadly understood to refer to connecting two or more elements, either directly or indirectly through intervening elements. Coupling (e.g., mechanical coupling) may be for any length of time, e.g., permanent or semi-permanent or only for an instant.

"A" and "an" as used herein indicate "at least one" of the item is present; a plurality of such items may be present, when possible. Spatially relative terms, such as "front," "back," "inner," "outer," "bottom," "top," "horizontal," "vertical," "upper," "lower," "side," "above," "below," "beneath," "upwardly," "outwardly," "inwardly," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context.

As used herein, substantially is defined as "to a considerable degree" or "proximate" or as otherwise understood by one ordinarily skilled in the art or as otherwise noted. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

One clinical classification of ERMs differentiates ERMs into three grades, with grade membranes not being associated with retinal or visual distortion, grade 1 membranes causing irregular wrinkling of the epiretinal surface caused by contraction of the ERM, and grade 2 membranes are thick membranes or macular puckers that cause profound retinal distortion and tractional phenomena. ADVANCES IN EYE SURGERY 116 (Patricio A. Pacheco ed., 2016). The extent of the visual effect is determined primarily by the degree of the induced retinal distortion, the position of the membrane in association to the macula, as well as the ERM's thickness and transparency. Id. at 118. Candidate patients that would benefit from the systems and methods disclosed herein would be those with grade 1 and grade 2 membranes causing significant visual distortion. Any patient being considered for a vitrectomy would first be offered the disclosed non-invasive treatment option. One study found that ERM progression was found in 28.6% of cases, stability was noticed in 38.8% of cases, and 25.7% of cases regressed after five years. Id. at 118. Accordingly, ERM is unlikely to spontaneously go away, although rare cases of spontaneous ERM separation from the retina have been documented. Id. In such cases with spontaneous ERM rupture or "peel", those patients are reported to have had significant improvement of vision. Hiroyasu Shirakawa & Nobuchika Ogino, *Idiopathic Epiretinal Membranes with Spontaneous Posterior Vitreous Separation,* 197 (2-3) OPHTHALMOLOGICA 90-94 (1987). To improve the patient's vision, it is not necessary to completely remove the ERM, but only to rupture the ERM. ERM separation from the retina would relax tension on the underlying retina that would be otherwise caused by the ERM, and such reduction in tension allows the retina to gradually unfold and flatten so that the retina will return to its approximate original configuration and the patient's vision can improve. The disclosed method aims to increase the likelihood that the ERM will regress/rupture.

Physicians generally advise against untested methods for treating ERM and tend to follow existing professional treatment processes. However, a patient hypothesized that non-invasive vibration may induce ERM rupture, thereby relaxing tension on the retina and allowing the retina to flatten to improve vision in patients whose vision is impaired due to an ERM causing waves in the retina. To test this hypothesis, repeated applications of vibration treatment were applied daily for several days, which indeed induced ERM rupture such that the ERM was dislodged from the retina and gradually floated downward in the vitreous fluid. Gradually, the patient's R eye vision improved from 20/60 to 20/30 as a result of retinal relaxation, and the patient's metamorphosis (wavy vision) also improved dramatically. Although existing professional treatment processes would not have advised using an untested treatment approach to induce ERM rupture, the findings could potentially be used to support a new non-invasive treatment method that could be used to treat ERMs. If this new treatment method could be attempted prior to performing a surgical procedure that includes a vitrectomy followed by peeling off the ERM, then this new treatment method could potentially avert many of the unwanted side effects or complications associated with this this surgical procedure. In accordance with the findings of this new treatment method, the systems and methods disclosed herein have been developed.

Figure 1A:
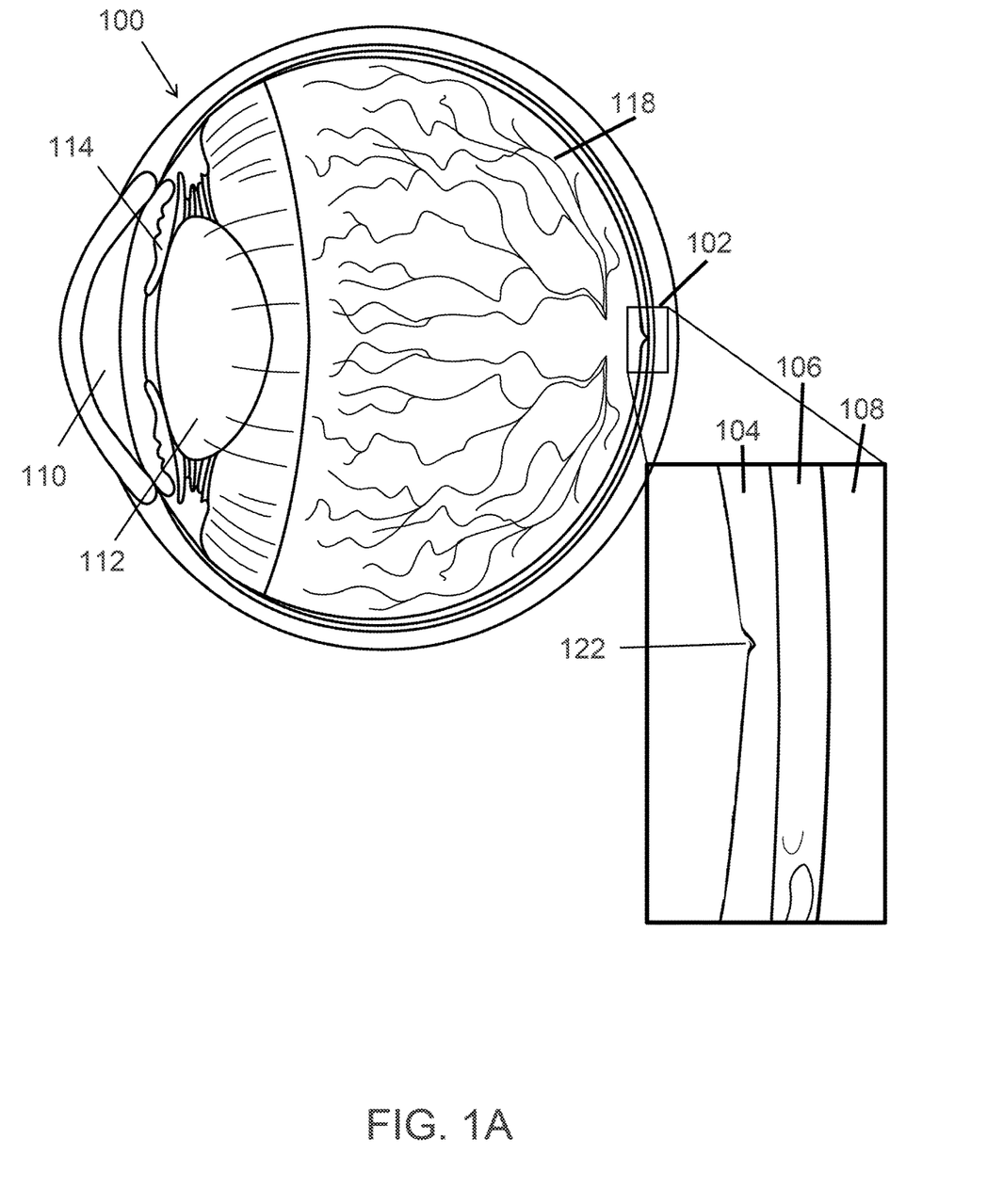
FIG. 1A illustrates a cross-sectional view of a relatively healthy eye with a magnified view of an example macular area, according to one embodiment.

FIG. 1A illustrates a cross-sectional view of the macular area 102 an eye 100, according to one embodiment. The eye 100 includes a vitreous 118, which is a gelatinous substance that fills the eye 100 and is loosely attached to the retina 104. The retina 104 is the innermost layer that converts light that enters the eye 100 into electrical signals. The choroid 106 is a thin layer of tissue between the retina 104 and the sclera 108 and is filled with blood vessels that provide oxygen and nutrients to the eye 100. The sclera 108 helps maintain the shape of the eye 100 and protects the inner layers from injury. The eye 100 also includes the anterior chamber 110, the lens 112, and the iris 114. Located near the center of the macular area 102 is the fovea 122, which is a small pit depicted as a v-shaped indentation that includes the largest concentration of cone photoreceptors where visual acuity is highest.

Figure 1B:
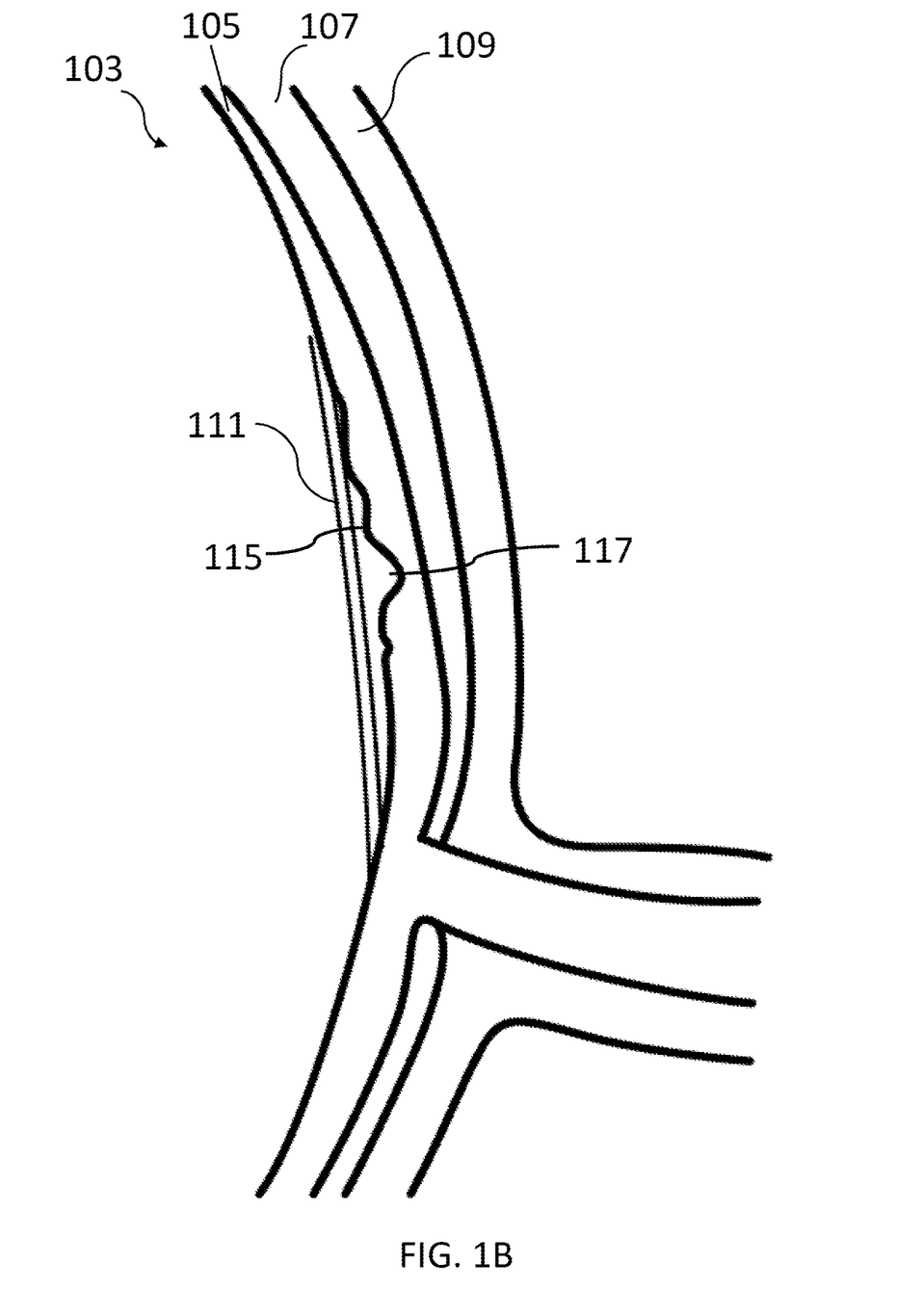
FIG. 1B illustrates a cross-sectional view of the macular area of an eye that includes an example ERM disposed on the retina creating folding and puckering of the underlying retina, according to one embodiment.

FIG. 1B illustrates a cross-sectional view of a macular area 103 of an eye that includes an example ERM 111 disposed on the retina 105, according to one embodiment. The ERM 111 is causing retinal folds 115 on the retina 105 and a macular pucker 117. The retina 105 is the innermost layer adjacent to the choroid 106, which is positioned in between the retina 105 and the sclera 109. As depicted, the ERM 111 can be a taut and thin membrane, which folds the underlying retina 105 into retinal folds 115 that have wave-like characteristics, which may cause wave-like distortions to the patient's vision.

Figure 2:
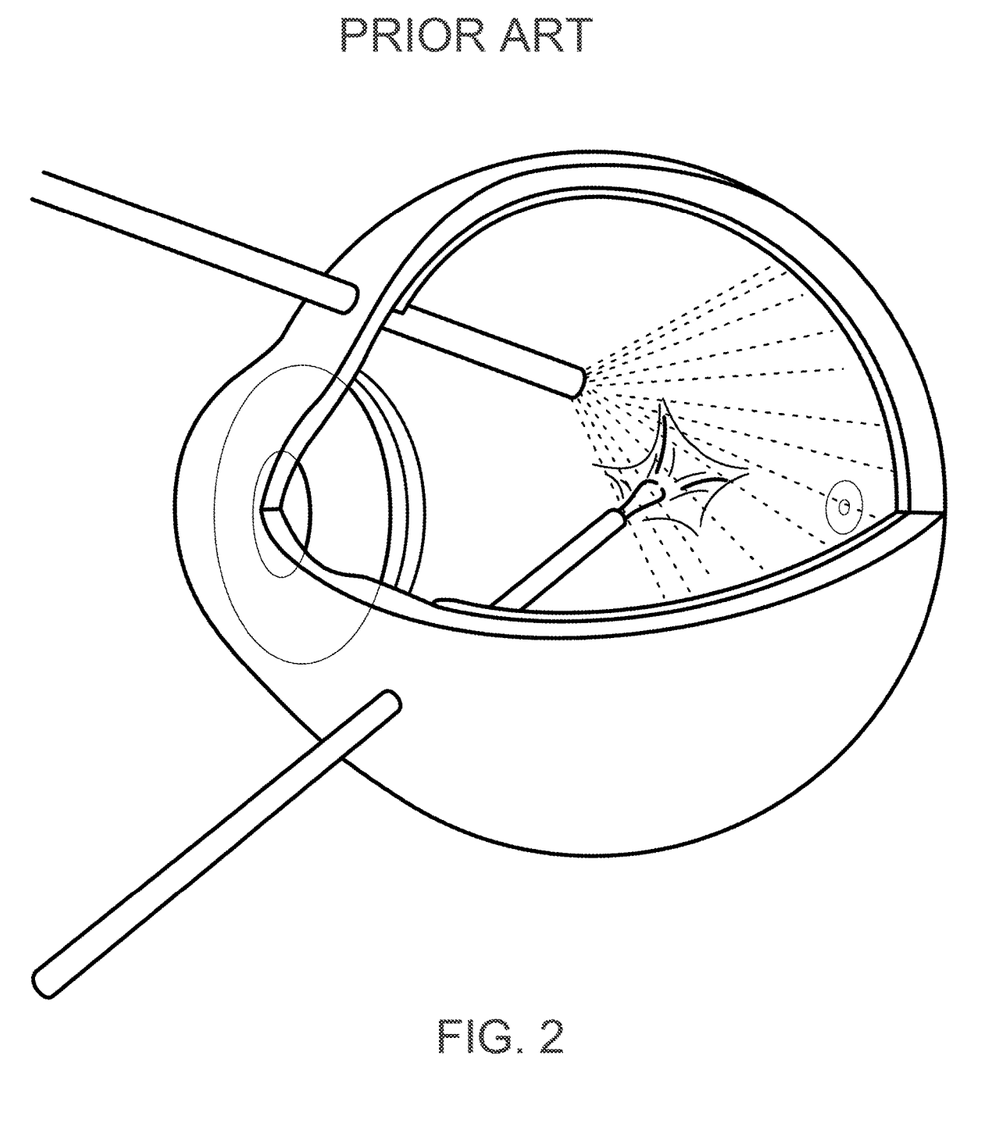
FIG. 2 depicts a prior art surgical removal of an example ERM disposed near the macular area of the retina, according to one embodiment.

FIG. 2 depicts a prior art surgical removal of an example ERM disposed near the macular area of the retina, according to one embodiment. The existing treatment commonly preferred for removal of the ERM involves vitrectomy (e.g., removal of vitreous gel and replacement with another solution) followed by peeling off the ERM with forceps. The replacement solution for the vitreous gel often involves a salt solution and may sometimes involve dyes. After the vitrectomy, the vitreous gel is naturally, but gradually, replaced with fluid produced by the body. The vitrectomy often involves tiny incisions to the eye in order to insert the forceps and a fiber optic light. After removal of the ERM, self-dissolving sutures may be used to close the incisions to the eye, or the small incisions may close and heal on their own without use of stitches. Generally, an eye patch is used to cover the eye until the next day and eye drops or ointment is used for several weeks. In general, about 75% of patients will have some improvement in vision as a result of the surgery. Vision often takes 3-6 months and sometimes a full year to improve to a new baseline vision. The improved vision may not be fully returned to pre-ERM levels. Due to the risks associated with this surgical procedure, the disclosed systems and methods were developed.

Figure 3A:
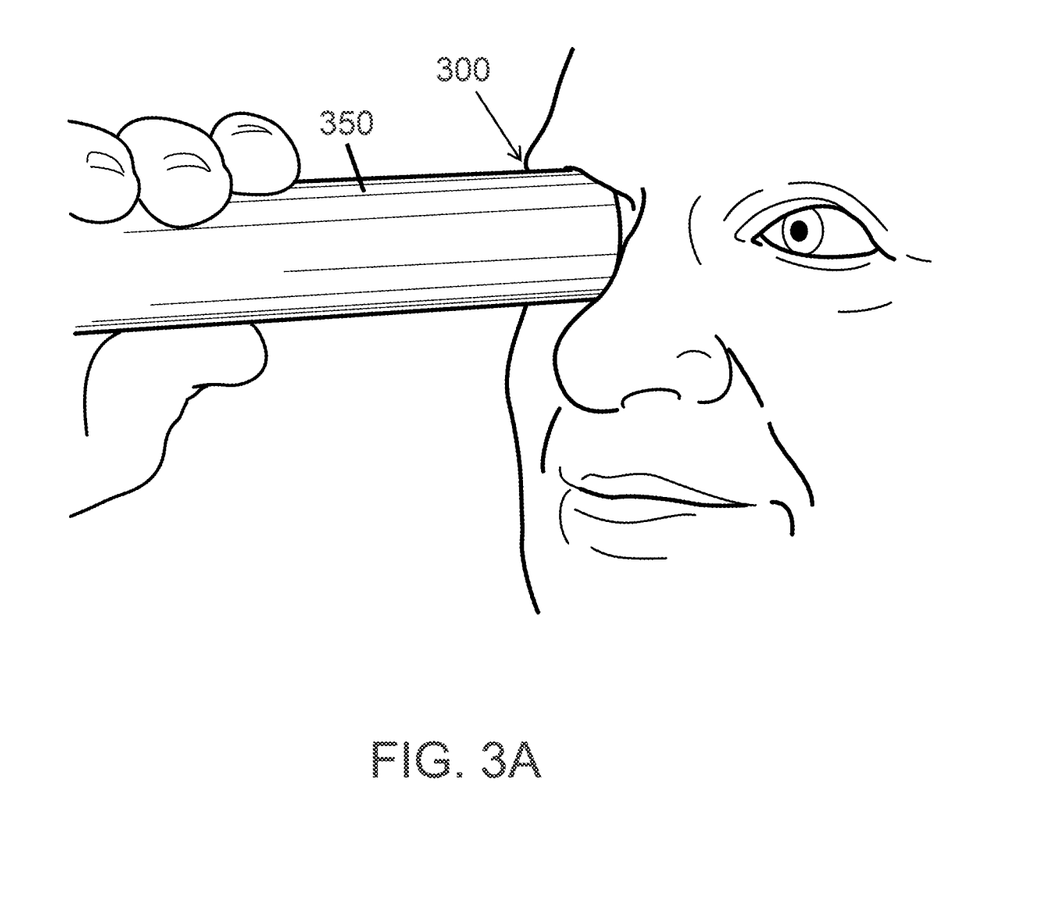
FIG. 3A illustrates an example vibrational device engaged with the eyelid of a patient, according to one embodiment.
Figure 3B:
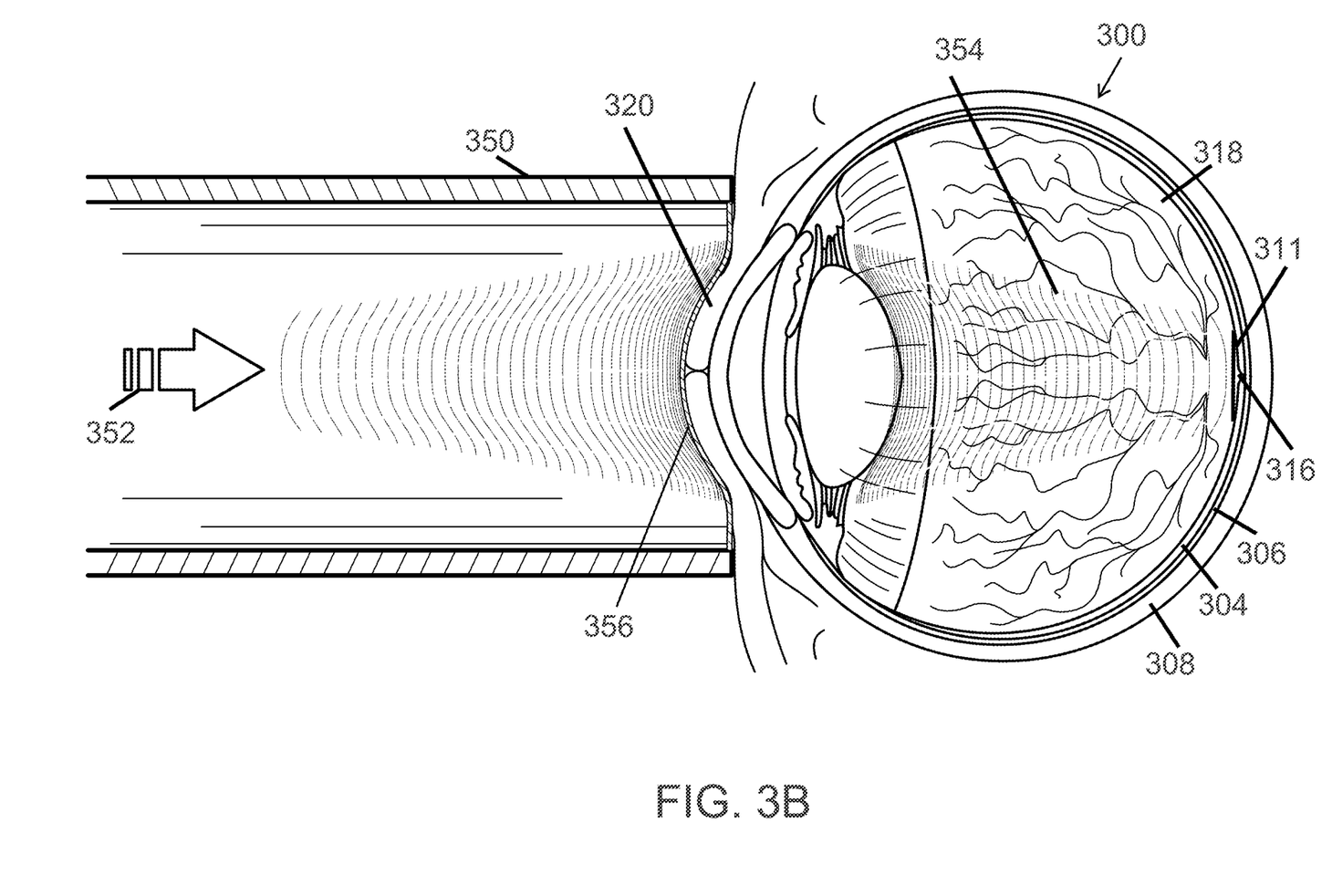
FIG. 3B depicts a vibrational force being applied, via an example vibrational device, to the eyelid of a patient, where the vibrational force is capable of propagating through the closed eyelid and eye to an ERM disposed on the retina of the eye, according to one embodiment.

FIGS. 3A and 3B illustrates an example vibrational device 350 engaged with the eyelid 320 of a patient, according to one embodiment. The eye 300 includes an ERM 311 disposed on the retina 304 and that is causing a macular pucker 316. The retina 304 is the innermost layer and is surrounded by the choroid 306 and sclera 308. In particular, FIG. 3B depicts a vibrational force 352 being applied to the eyelid 320 where the vibrational force 352 is capable of propagating through waves 354 through the closed eyelid 320 to an ERM 311 disposed on the epiretinal surface of the retina 304 of the eye 300. In some instances, the vibrational force 352 may include a percussive force having an up-and-down motion, whereas other times the vibrational force 352 may be less ballistic. The waves 354 may pass through the anterior chamber, iris, lens, and vitreous 318 before impacting the ERM 311. In order to provide vibration induced membrane rupture to the ERM 311, an interface 356 of the vibrational device may be engaged with the closed eyelid 320 of the patient while a vibrational force 352 is applied. According to one embodiment, the vibrational device 350 may include a support (i.e., handle) extending outward from the interface 356 across at least a portion of a length of the vibrational device 350, and may be used to facilitate steadying the interface 356 during engagement with the closed eyelid 320. The vibrational device 350 may be configured to produce a plurality (e.g., 4-5) of vibration frequencies.

In some non-limiting embodiments, it is contemplated that the waves 354 may provide harmonic resonance, where the harmonic frequency produced by the vibrational force 352 is equal or very close to a natural resonant frequency of the ERM. The resonance frequency is that which produces a wavelength that approximates the size of the ERM. For instance, in one non-limiting example, the resonance frequency may be calculated using the following equation:

$$\text{Resonance Frequency}\left(\text{in Hz or } \frac{\text{beats}}{\text{second}}\right) = \frac{\text{Speed of sound in vitreous}\left(1500 \; \frac{\text{meters}}{\text{second}} \text{ for water}\right)}{\text{size of the } ERM (\text{in meters})}.$$

It is possible that if the vibrational force 352 is applied in such a manner that the harmonic resonance of the vibrational force 352 causes waves 354 that are very similar to or the same as the harmonic resonance of the ERM, then this may cause the ERM 311 to rupture or otherwise at least partially dislodge from the retina 304 of the eye 300. However, it is also possible that the ERM rupture caused by the vibrational force 352 is unrelated to harmonic resonance and induces membrane rupture independently of harmonic resonance. Vibration induced membrane rupture is entirely different than shock wave therapy, which uses short-duration, high-energy shockwaves to treat stones (i.e., pulverize) in the kidneys (e.g., via shock wave lithotripsy), since shock wave therapy uses direct mechanical forces and indirect cavitation gas bubbles that subsequently implode at high speeds. Vibration induced membrane rupture is also unlike a high-frequency focused ultrasound (HIFU), in which heat generated by high frequency sound waves is used to destroy malignant tumors.

In contrast to these existing techniques, vibration induced membrane rupture utilizes relatively low vibration frequencies without high-energy shockwaves. Rather, vibration induced membrane rupture would incorporate a series of mild intensity vibrations for a first instance (e.g., approximately two minutes), and potentially followed up by one or more additional instances. If desired, rest period(s) may be implemented between each instance. In some embodiments, the vibrational device 350 may be operated by a retinologist, and most patients would not need sedation. A single treatment would incorporate multiple instances of vibration, and each instance of vibration may have the same frequency or have gradually increasing frequencies. The patient would then be discharged and return another day (e.g., after one week) for reassessment. At that visit, the patient may then be observed using an observational device (e.g., using a fundus biomicroscopy or optical coherence tomography (OCT)) that is configured to inspect at least the retina 304 of the eye 300 once one or more instances of the vibrational force 352 is applied to determine whether the vibrational force 352 induced rupture of the ERM 311 sufficient to at least partially dislodge the ERM 311 from the retina 304 of the eye 300. If the ERM 311 had ruptured or started to rupture, the patient would either be observed or an additional vibrational treatment could be given, at the discretion of the retinologist. Alternatively, if the ERM was unchanged, another application of vibration induced membrane rupture treatment could be applied at a higher intensity with either the same frequency(s) or at a different frequency than the prior application. The number of applications can vary, depending on the desired treatment regimen of the retinologist. After a series of applications, if the ERM 311 has still not ruptured or otherwise become at least partially detached from the retina 304, then the patient would be given the option of obtaining a vitrectomy with surgical removal of the ERM 311.

Figure 4:
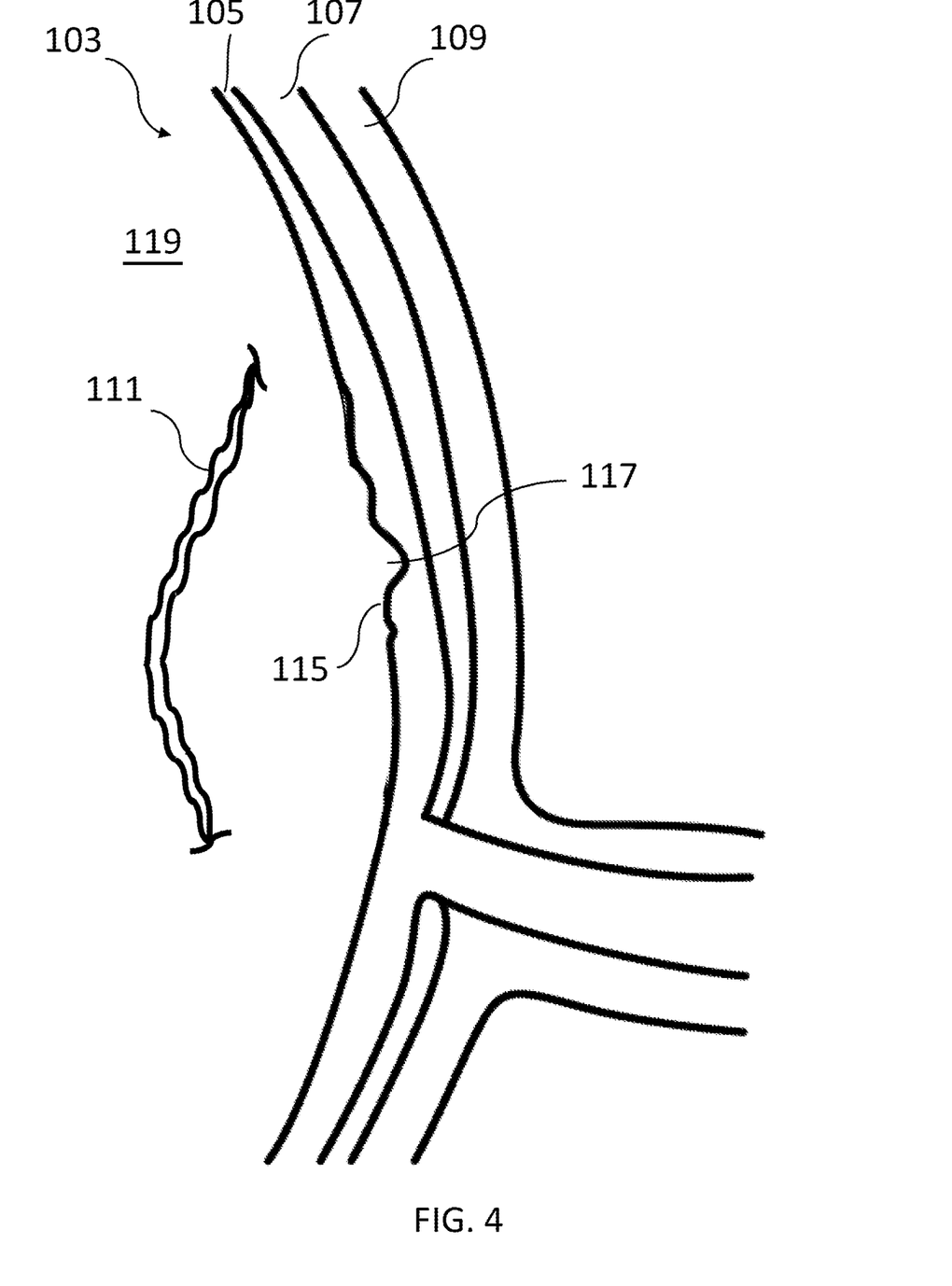
FIG. 4 depicts a cross-sectional view of the macular area of the eye of FIG. 1B where the example ERM has been dislodged from the retina and is floating in vitreous membrane, according to one embodiment.

FIG. 4 depicts a cross-sectional view of the macular area 103 of the eye of FIG. 1B where the example ERM 111 has been dislodged from the retina 105 and is floating in vitreous membrane 119, according to one embodiment. In this embodiment, the patient could see a "floater" in the affected eye; however, over time that "floater" would sink, due to gravitational force, out of the visual pathway to the inferior globe of the eye such that the patient would no longer visually see the "floater". The retina 105 is the innermost layer adjacent the choroid 106, which is positioned in between the retina 105 and the sclera 109. After one or more instances and/or applications of a vibration induced membrane rupture treatment, the ERM 111 may rupture or otherwise at least partially dislodge from the epiretinal surface of the retina 105. The macular pucker 117 does not change vision much immediately, but over the succeeding weeks and months the retina should flatten out and unfold close to its normal state. As it does, the patient's visual acuity and the symptoms of metamorphosis (wavy vision) should improve.

Figure 5:
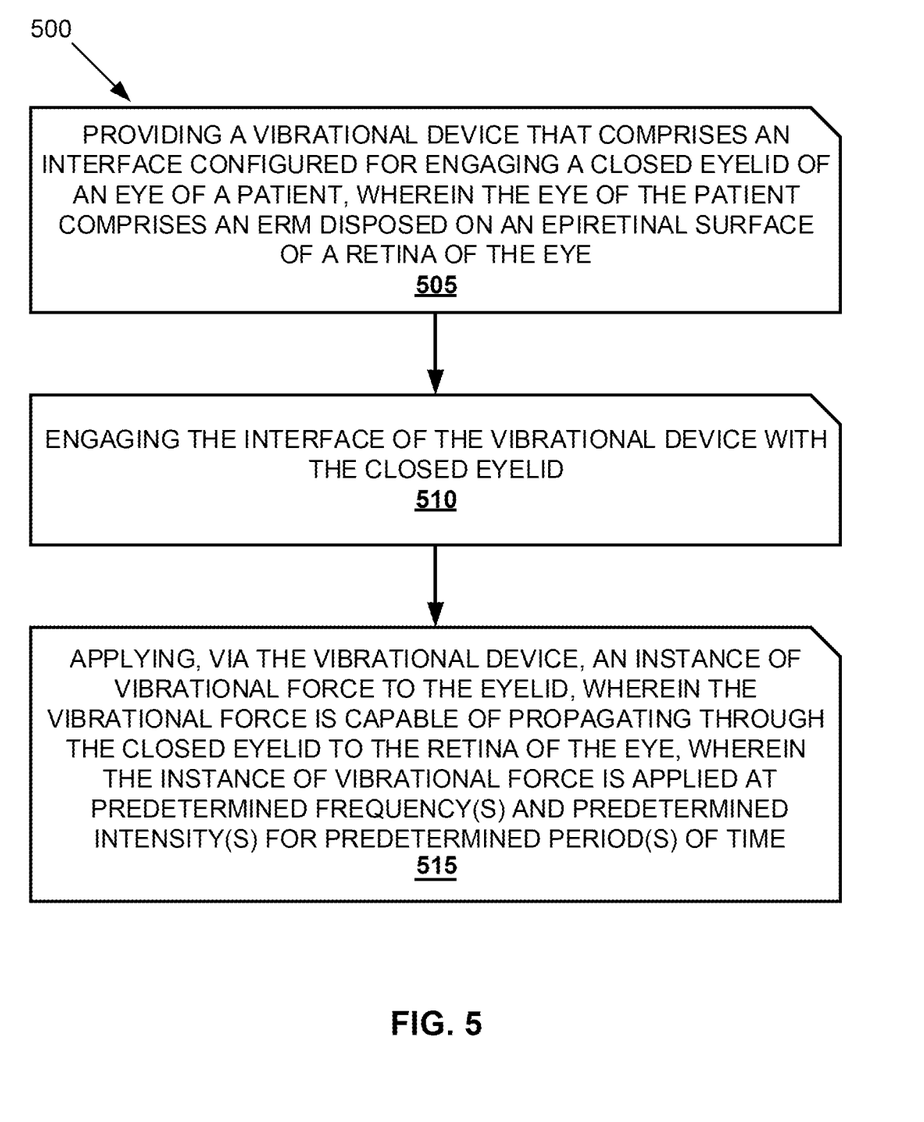
FIG. 5 depicts a block diagram of an example method for ERM treatment, according to one embodiment.

FIG. 5 depicts a block diagram of an example method 500 for ERM treatment, according to one embodiment. At block 505, a vibrational device that includes an interface configured for engaging a closed eyelid of an eye of a patient is provided, where the eye of the patient includes an ERM disposed on an epiretinal surface of a retina of the eye. At block 510, the interface of the vibrational device is engaged with the closed eyelid. Further, at block 515, while the interface is engage with the closed eyelid an instance of vibrational force is applied, via the vibrational device, to the eyelid, where the vibrational force is capable of propagating or otherwise configured to propagate through the closed eyelid, the anterior chamber, the iris, the lens, and the vitreous fluid to the retina of the eye. The instance of vibrational force is applied at one or more predetermined frequencies and one or more predetermined intensities for one or more predetermined periods of time. In some embodiments, the one or more predetermined frequencies and one or more predetermined intensities for the one or more predetermined periods of time is based on a prediction or hypothesis for the vibrational force (both the intensity and frequency) needed to induce rupture of the ERM such that the ERM is at least partially dislodged from the retina of the eye. In some embodiments, the vibrational device may be configured to provide a plurality of predetermined vibration frequencies and/or intensities, or more particularly at least three vibration frequencies.

According to various embodiments, the instance is a first instance and the engaging and applying are repeated in temporal succession for one or more additional instances. In some applications, a rest period immediately follows the first instance as well as each of the one or more additional instances. In some examples, each of the one or more additional instances include the one or more predetermined frequencies and one or more intensities are applied in a series. In this type of example, every instance uses the same frequency (e.g., a predetermined frequency) and intensity for a predetermined period of time (e.g., two minutes) with rest periods in between. In other examples, each of the one or more additional instances include a different frequency and/or intensity such that each instance increases in frequency and/or intensity during the application. For example, a relatively low frequency and/or intensity may be applied for a predetermined period of time (e.g., two minutes) and may optionally be followed by a short rest period (e.g., 10 seconds-2 minutes) followed by another instance at a relatively higher frequency and/or intensity than the last instance. This process is repeated for a given number of frequencies (e.g., 4-5 different frequencies) and/or intensities for that treatment application.

In some embodiments, the first instance and one or more additional instances make up a first treatment application on a first day. If the initial session using the first instance and one or more additional instances does not produce ERM rupture, one or more additional treatment applications are applied on one or more additional days. In some embodiments in which a single frequency and/or intensity is applied for all instances during the first application, each of the one or more additional treatment applications may have a respective frequency and/or intensity that differs from the one or more predetermined frequencies and/or intensities and is applied for a plurality of instances that are repeated in temporal succession. For example, each of the one or more treatment applications may include a progressively increasing frequency and/or intensity such that each respective treatment includes a respective frequency and/or intensity that is greater than an immediately prior treatment application. The treatment applications may continue until a maximum tolerable intensity is applied, where the maximum tolerable intensity is determined based on medical evaluation.

In some embodiments, after the first treatment application an observation assessment of the eye is performed to determine whether the first treatment application induced rupture of the ERM sufficient to at least partially dislodge the ERM from the retina of the eye. Further, based on determining the first treatment application did not induce rupture of the ERM to sufficient to at least partially dislodge the ERM from the retina of the eye, at least one additional treatment application of the one or more additional treatment applications may be performed. For treatments in which there are multiple treatment applications on separate days, the observation assessment may be repeated after each respective treatment application to observe any changes to the ERM. Some example observation assessment techniques may include optical coherence tomography (OCT), which is a non-invasive imaging test that uses light waves to take cross-sectional images of the retina.

Also disclosed herein is an ERM treatment system that includes an interface configured for engaging a closed eyelid of an eye of a patient, where the eye of the patient includes an ERM disposed on an epiretinal surface of a retina of the eye. The system also includes a motor configured to provide a vibrational force via the interface. In some embodiments, the motor may include an eccentric rotating mass vibration motor that incorporates an offset or non-symmetric mass that rotates such that the centripetal force of the offset mass results in a displacement of the motor. When there is a high number of revolutions per minute, the motor is continuously being displaced by asymmetric forces and this is perceived as vibration. When the interface is engaged with the closed eyelid, an instance of vibrational force is applied to the eyelid, where the vibrational force is capable and/or otherwise is configured to propagate through the closed eyelid, the iris, the lens, and the vitreous fluid to the retina of the eye. Further, the instance of vibrational force is applied at one or more predetermined frequencies and one or more predetermined intensities for one or more predetermined periods of time. According to various embodiments, the vibrational force produced by the vibrational device include a range of vibrations at different frequencies. For example, the vibration frequencies may have a low frequency range of 5-10 kHz, various intermediate frequencies, and a high frequency range of 150-300 kHz. Thus, the vibrational device may be configured to produce vibrations anywhere between about 5 kHz to about 180 kHz.

The ERM treatment system may also include a housing that extends from the interface and provides a handle or other support that is configured to facilitate steadying the interface during engagement with the closed eyelid. Further, the housing may encase the motor. During treatment, the vibrational device may be handheld by the retinologist or alternatively by a mechanical arm that would be linked with a device to hold the patient's head in a steady position.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises," "has," "includes" or "contains" one or more steps or elements possesses those one or more steps or elements, but is not limited to possessing only those one or more steps or elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

In the flowchart illustrations and/or block diagrams disclosed herein, each block in the flowchart/diagrams may represent a module, segment, or portion of a method. In some implementations, the functions noted in the blocks may occur out of the order noted in the Figures. For example, two blocks shown in succession may, in fact, be executed substantially concurrently, or the blocks may sometimes be executed in the reverse order, depending upon the functionality involved.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. An epiretinal membrane (ERM) treatment method comprising:
   providing a vibrational device that comprises an interface configured for engaging a closed eyelid of an eye of a patient, wherein the eye of the patient comprises an ERM disposed on an epiretinal surface of a retina of the eye;
   engaging the interface of the vibrational device with the closed eyelid; and
   applying, via the vibrational device while the interface is engaged with the closed eyelid, an instance of vibrational force to the eyelid, wherein the vibrational force is propagated through the closed eyelid to the ERM disposed on the epiretinal surface of the retina of the eye;
   wherein the instance of vibrational force is applied at one or more predetermined frequencies and one or more predetermined intensities for one or more predetermined periods of time, wherein the instance of vibrational force is applied to directly dislodge the ERM from the epiretinal surface of the retina of the eye through mechanical means.

2. The treatment method of claim 1, wherein the one or more predetermined frequencies, one or more predetermined intensities, and one or more predetermined periods of time are based on a prediction for the vibrational force needed to induce rupture of the ERM such that the ERM is at least partially dislodged from the retina of the eye.

3. The treatment method of claim 1, wherein the instance is a first instance and wherein the engaging and applying are repeated in temporal succession for one or more additional instances based on the ERM not being dislodged by the first instance.

4. The treatment method of claim 3, wherein a rest period immediately follows the first instance as well as each of the one or more additional instances.

5. The treatment method of claim 3, wherein each of the one or more additional instances comprise one or more respective predetermined frequencies and one or more respective predetermined intensities, wherein the first instance applied at the one or more predetermined frequencies and the one or more predetermined intensities and the one or more respective predetermined frequencies and the one or more respective predetermined intensities of each of the one or more additional instances are applied in a series.

6. The treatment method of claim 5, wherein the first instance and the one or more additional instances comprise a first treatment application on a first day, and wherein one or more additional treatment applications are applied on one or more additional days, the one or more additional treatment applications each having a respective intensity that is applied for a plurality of instances repeated in temporal succession.

7. The treatment method of claim 6, wherein each of the one or more additional treatment applications comprise a progressively increasing intensity that is greater than an immediately prior treatment application.

8. The treatment method of claim 6, wherein the treatment method further comprises:

performing, after the first treatment application, an observation assessment of the eye to determine whether the first treatment application induced rupture of the ERM sufficient to at least partially dislodge the ERM from the retina of the eye; and based on determining the first treatment application did not induce rupture of the ERM to sufficient to at least partially dislodge the ERM from the retina of the eye, performing at least one additional treatment application of the one or more additional treatment applications.

9. The treatment method of claim 8, wherein the treatment method further includes repeating the observation assessment after each respective treatment application of the one or more additional treatment applications.

10. The treatment method of claim 8, wherein the observation assessment comprises optical coherence tomography.

11. The treatment method of claim 8, wherein the plurality of predetermined vibration frequencies comprise at least three vibration frequencies.

12. The treatment method of claim 1, wherein the vibrational device is configured to provide a plurality of predetermined vibration frequencies and a plurality of predetermined intensities.

* * * * *